US012678395B2

(12) United States Patent
Wu et al.

(10) Patent No.: US 12,678,395 B2
(45) Date of Patent: Jul. 14, 2026

(54) SOLID CLEANSING COMPOSITIONS AND METHODS FOR THE SAME

(71) Applicant: Colgate-Palmolive Company, New York, NY (US)

(72) Inventors: Qiang Wu, Hillsborough, NJ (US); Shujiang Cheng, Warren, NJ (US); Juliana Nwosisi, Scotch Plains, NJ (US); Laurence Du-Thumm, Princeton, NJ (US)

(73) Assignee: Colgate-Palmolive Company, New York, NY (US)

( * ) Notice: Subject to any disclaimer, the term of this patent is extended or adjusted under 35 U.S.C. 154(b) by 972 days.

(21) Appl. No.: 17/250,893

(22) PCT Filed: Sep. 24, 2018

(86) PCT No.: PCT/US2018/052440
§ 371 (c)(1),
(2) Date: Mar. 22, 2021

(87) PCT Pub. No.: WO2020/068034
PCT Pub. Date: Apr. 2, 2020

(65) Prior Publication Data
US 2021/0267878 A1        Sep. 2, 2021

(51) Int. Cl.
| *A61K 8/92* | (2006.01) |
| *A61K 8/36* | (2006.01) |
| *A61K 8/64* | (2006.01) |
| *A61Q 19/00* | (2006.01) |
| *A61Q 19/10* | (2006.01) |

(52) U.S. Cl.
CPC .............. *A61K 8/922* (2013.01); *A61K 8/361* (2013.01); *A61K 8/64* (2013.01); *A61Q 19/007* (2013.01); *A61Q 19/10* (2013.01)

(58) Field of Classification Search
None
See application file for complete search history.

(56) References Cited

U.S. PATENT DOCUMENTS

| 4,148,743 A | 4/1979 | Schubert |
| 5,314,873 A | 5/1994 | Tomita et al. |
| 6,664,217 B1 | 12/2003 | Puvvada et al. |
| 2001/0014315 A1 | 8/2001 | Harbeck |
| 2008/0286390 A1 | 11/2008 | Tanyi |
| 2014/0349903 A1 | 11/2014 | Winston et al. |
| 2017/0348203 A1 | 12/2017 | Schelges et al. |

FOREIGN PATENT DOCUMENTS

| CA | 1094910 | | 2/1981 |
| CA | 2658356 | * | 4/2008 |
| CN | 104651087 | | 5/2015 |
| CN | 111214939 | | 6/2020 |
| IE | 47936 B1 | * | 7/1984 |
| JP | H09-131393 | | 5/1997 |
| RU | 2016117904 | | 11/2017 |
| WO | WO 98/55094 | * | 12/1998 |
| WO | 2003/042346 | | 5/2003 |
| WO | 2007/025645 | | 3/2007 |
| WO | 2009/082790 | | 7/2009 |
| WO | 2018/030983 | | 2/2018 |
| WO | 2019/117858 | | 6/2019 |
| WO | 2020/068034 | | 4/2020 |

OTHER PUBLICATIONS

6 Benefits of Flaxseed oil-Plus How to use it, Sep. 2017, 18 pages.*
International Search Report and the Written Opinion of the International Searching Authority issued in International Application PCT/US2018/052440 mailed Jan. 3, 2019.
Colorist Christophe Robin, 2017, "Hydrating Shampoo Bar", Mintel Database GNPD AN: 5044723.
International Search Report and the Written Opinion of the International Searching Authority issued in International Application PCT/US2022/037989 mailed Dec. 6, 2022.
1997, Google english translation of JPH09131393A.
2020, Google english translation of CN111214939A.
Socialite Beauty & Wellness, "The Benefits of Flaxseed Oil." Socialite Beauty & Wellness Official Website, (Nov. 4, 2019), https://socialitebeauty.ca/blogs/cleanbeautyguide/flax-seed-oil. [retrieved from the Internet on Feb. 13, 2026], pp. 1-5.
Tamtaji, O. et al., "Effects of flaxseed oil supplementation on biomarkers of inflammation and oxidative stress in patients with metabolic syndrome and related disorders: A systematic review and meta-analysis of randomized controlled trials", Clinical Nutrition ESPEN, 40, pp. 27-33, https://doi.org/10.1016/j.clnesp.2020.09.017 Nov. 9, 2020 (Sep. 11, 2020).
Colgate-Palmolive, 2020, "Anti-Bacterial Bar Soap", Mintel Database GNPD AN: 8274017.

(Continued)

*Primary Examiner* — Michael V Meller

(57) ABSTRACT

Solid cleansing compositions and methods for the same are disclosed herein. The solid cleansing compositions may include a soap, a plant oil, and a hydrolyzed protein. The plant oil and the hydrolyzed protein may be present in an effective amount to maintain or increase hydration of skin. The plant oil may be or include a flaxseed oil, and the hydrolyzed protein may be or include a hydrolyzed milk protein.

1 Claim, No Drawings

(56)          References Cited

OTHER PUBLICATIONS

Erno Laszlo, 2020, "Hydrate & Nourish Gel Cream", Mintel Database GNPD AN: 7609235.

Laboratorium Kosmetyczne Dr. Irena Eris, 2021, "Moisturising Eco Body Lotion", Mintel Database GNPD AN: 8500885.

Natura Siberica, 2019, "Soap for Deep Facial Cleansing", Mintel Database GNPD AN: 6812861.

Prakritik Agrichem, 2019, "Flaxseed Essential Oil", Mintel Database GNPD AN: 6720805.

UpCircle, 2020, "Body Cream", Mintel Database GNPD AN: 8147859

* cited by examiner

SOLID CLEANSING COMPOSITIONS AND METHODS FOR THE SAME

BACKGROUND

Cosmetic and personal care compositions, such as bar soaps, may often include one or more ingredients that may strip moisture from skin, thereby leaving the skin feeling overly dry or chapped. Accordingly, conventional cosmetic and personal care compositions may often include moisturizers, such as glycerin, to promote or maintain hydration of the skin. While these moisturizers have demonstrated efficacy in promoting the hydration of the skin, they are typically only incorporated into non-solid or liquid cosmetic and personal care compositions (e.g., gels, creams, lotions, liquids, etc.), as the incorporation of these moisturizers into solid cosmetic and personal care compositions, such as bar soaps, in effective or appreciable quantities has proven to be challenging.

What is needed, then, are improved solid cleansing or cosmetic and personal care compositions and methods for maintaining or increasing hydration of skin.

BRIEF SUMMARY

This summary is intended merely to introduce a simplified summary of some aspects of one or more implementations of the present disclosure. Further areas of applicability of the present disclosure will become apparent from the detailed description provided hereinafter. This summary is not an extensive overview, nor is it intended to identify key or critical elements of the present teachings, nor to delineate the scope of the disclosure. Rather, its purpose is merely to present one or more concepts in simplified form as a prelude to the detailed description below.

The foregoing and/or other aspects and utilities embodied in the present disclosure may be achieved by providing a solid cleansing composition including a soap, a plant oil, and a hydrolyzed protein. The plant oil and the hydrolyzed protein may be present in an effective amount to maintain or increase hydration of skin.

In at least one implementation, the plant oil includes flaxseed oil. In another implementation, the plant oil consists essentially of flaxseed oil, and omits one or more other plant oils that may increase or decrease hydration of skin.

In at least one implementation, the hydrolyzed protein includes hydrolyzed milk protein, optionally, the hydrolyzed milk protein is present in an amount of from greater than 0 weight % to about 1 weight %, optionally, from about 0.15 weight % to about 0.3 weight %, further optionally, from about 0.2 weight % to about 0.25 weight %, based on a total weight of the solid cleansing composition.

In at least one implementation, the plant oil is present in an amount of from greater than 0 weight % to less than or equal to 5 weight %, optionally, in an amount of from greater than 0 weight % to less than or equal to 1 weight %, further optionally, in an amount of about 0.5 weight %.

In at least one implementation, a weight ratio of the plant oil to the hydrolyzed protein is about 2.0:1 to about 2.5:1, optionally, about 2.1:1 to about 2.4:1, about 2.2:1 to about 2.3:1, or about 2.27:1.

In at least one implementation, the soap includes sodium soap, optionally the soap further includes one or more of an ammonium soap, a potassium soap, a magnesium soap, and a calcium soap In at least one implementation, the hydrolyzed protein is provided by an aqueous hydrolyzed protein solution including hydrolyzed milk protein and water, optionally, the hydrolyzed milk protein is present in an amount of from about 18 weight % to about 25 weight % or about 20 weight % to about 23 weight %, based on a total weight of the aqueous hydrolyzed protein solution.

In at least one implementation, the soap includes alkali metal salts of aliphatic acids having 8 to 22 carbon atoms.

In at least one implementation, the solid cleansing composition further includes one or more humectants, optionally, the one or more humectants are selected from ascorbic acid, ascorbyl dipalmitate, acetamide MEA, glucose glutamate, glucuronic acid, TEA-lactate, TEA-PCA, corn syrup, fructose, glucose, glycerin, glycol, 1,2,6-hexanetriol, sodium lactate, sodium PCA, hydrogenated starch hydrolysate, inositol, lactic acid, lactose, mannitol, PCA, PEG-10 propylene glycol, polyamino sugar condensate, propylene glycol, pyridoxine dilaurate, saccharide hydrolysate, hydroxystearyl methylglucamine, glucamine, maltitol, mannitol, methyl gluceth-10, methyl gluceth-20, riboflavin, PEG-4, PEG-6, PEG-8, PEG-9, PEG-10, PEG-12, PEG-14, PEG-16, PEG-18, PEG-20, PEG-32, PEG-40, glutamic acid, glycereth-7, glycereth-12, glycereth-26, saccharide isomerate, sorbeth-20, sorbitol, sucrose, thioglycerin, tris-(hydroxymethyl) nitromethane, tromethamine, histidine, PEG-75, PEG-135, PEG-150, PEG-200, PEG-5 pentaerythritol ether, polyglyceryl sorbitol, sorbitol, urea, xylitol, and combinations thereof.

In at least one implementation, the solid cleansing composition further includes one or more free fatty acids, optionally, wherein the one or more free fatty acids are selected from palm kernel oil, palm oil, coconut oil, olive oil, laurel oil, and combinations thereof.

In at least one implementation, the solid cleansing composition is a bar soap.

The foregoing and/or other aspects and utilities embodied in the present disclosure may be achieved by providing a method for maintaining or increasing hydration of skin of a user. The method may include contacting any one of the solid cleansing compositions disclosed above or herein with the skin of the user in need thereof.

The foregoing and/or other aspects and utilities embodied in the present disclosure may be achieved by providing any one of the solid cleansing compositions disclosed above or herein for use in maintaining or increasing hydration of skin.

The foregoing and/or other aspects and utilities embodied in the present disclosure may be achieved by providing a method for preparing a solid cleansing composition. The method may include contacting an effective amount of a plant oil and an effective amount of hydrolyzed protein with one another to prepare a mixture. The method may further include contacting a soap with the mixture. In at least one implementation, the effective amounts of the plant oil and the hydrolyzed protein is an amount effective to maintain or increase hydration of skin, optionally, wherein the plant oil comprises flaxseed oil, further optionally, wherein the hydrolyzed protein comprises hydrolyzed milk protein.

In at least one implementation, the plant oil may be present in an amount of from greater than 0 weight % to less than or equal to 1 weight %, and wherein the hydrolyzed protein is present in an amount of from greater than 0 weight % to less than or equal to 2 weight %, based on a total weight of the solid cleansing composition.

Further areas of applicability of the present disclosure will become apparent from the detailed description provided hereinafter. It should be understood that the detailed description and specific examples, while indicating some typical aspects of the disclosure, are intended for purposes of illustration only and are not intended to limit the scope of the disclosure.

DETAILED DESCRIPTION

The following description of various typical aspect(s) is merely exemplary in nature and is in no way intended to limit the disclosure, its application, or uses.

As used throughout, ranges are used as shorthand for describing each and every value that is within the range. Any value within the range may be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Additionally, all numerical values are "about" or "approximately" the indicated value, and take into account experimental error and variations that would be expected by a person having ordinary skill in the art. It should be appreciated that all numerical values and ranges disclosed herein are approximate values and ranges, whether "about" is used in conjunction therewith. It should also be appreciated that the term "about," as used herein, in conjunction with a numeral refers to a value that may be ±0.01% (inclusive), ±0.1% (inclusive), ±0.5% (inclusive), ±1% (inclusive) of that numeral, ±2% (inclusive) of that numeral, ±3% (inclusive) of that numeral, ±5% (inclusive) of that numeral, ±10% (inclusive) of that numeral, or ±15% (inclusive) of that numeral. It should further be appreciated that when a numerical range is disclosed herein, any numerical value falling within the range is also specifically disclosed.

The present inventors have surprisingly and unexpectedly discovered that solid bar soap compositions including a synergistic combination of flaxseed oil and hydrolyzed milk protein, both of which separately and individually decreased the relative water content or hydration of skin, significantly increased the hydration of skin when utilized in combination with one another. It was further discovered that the synergistic effects of the flaxseed oil and the hydrolyzed milk protein were present at relatively low concentrations of the hydrolyzed milk protein.

Compositions

Compositions disclosed herein may be or include solid cleansing compositions. Illustrative solid cleansing compositions may be or include, but are not limited to, bar soap compositions, cleansing bars, and other solid cleansing compositions that may be used for personal cleansing or as a laundry bar. The solid cleansing compositions may include one or more plant oils and one or more hydrolyzed proteins in an amount sufficient to increase hydration or water content of skin. Particularly, as further described herein, the solid cleansing composition may include flaxseed oil and hydrolyzed milk protein in synergistic amounts to increase hydration of skin.

Plant Oil

The solid cleansing composition may include one or more plant oils. As used herein, "plant oil" may refer to oil that is obtained from a plant, or manufactured oil made by blending at least two components of oil (e.g., triglycerides, saturated and/or unsaturated fatty acids, etc.) to substantially mimic the composition of a natural plant oil or provide an oil substantially similar in composition to a plant oil. For example, a manufactured oil substantially similar in composition to a plant oil may include at least 50 weight %, at least 60 weight %, at least 70 weight %, at least 80 weight %, at least 90 weight %, at least 95 weight %, at least 98 weight %, at least 99 weight %, at least 99.5 weight %, at least 99.9 weight %, or 100 weight % of the components that are naturally found in the plant oil that the manufactured oil is designed to substantially mimic.

Illustrative plant oils may be or include, but are not limited to, palm kernel oil, coconut oil, avocado oil, canola oil, corn oil, cottonseed oil, olive oil, palm oil, high-oleic sunflower oil, mid-oleic sunflower oil, sunflower oil, palm stearin oil, palm kernel olein oil, safflower oil, babassu oil, sweet almond oil, castor oil, canola oil, soybean oil, olive oil, acai oil, andiroba oil, apricot kernel oil, argan oil, passion fruit oil, marula oil, mango oil, shea oil, macadamia nut oil, brazil nut oil, borage oil, copaiba oil, grape seed oil, buriti oil, sesame oil, flaxseed oil or linseed oil, blueberry oil, cranberry oil, blackberry oil, plum oil, raspberry oil, camelina oil, *camellia* oil, walnut oil, wheat germ oil, calendula oil, cherry kernel oil, cucumber seed oil, *papaya* oil, aloe vera oil, hemp oil, and the like, and mixtures or combinations thereof. In a preferred implementation, the plant oil includes flaxseed or linseed oil.

The amount or concentration of the one or more plant oils present in the solid cleansing composition may vary widely. In at least one implementation, the amount of the one or more plant oils present in the solid cleansing composition may be from greater than 0 weight % to less than or equal to 5 weight %, based on a total weight of the solid cleansing composition. For example, the amount of the one or more plant oils present in the solid cleansing composition may be from greater than 0 weight %, about 0.5 weight %, about 1 weight %, about 1.5 weight %, about 2 weight %, or about 2.5 weight % to about 3 weight %, about 3.5 weight %, about 4 weight %, about 4.5 weight %, or about 5 weight %. In another example, the amount of the one or more plant oils present in the solid cleansing composition may be from greater than 0 weight % to about 5 weight %, about 0.5 weight % to about 4.5 weight %, about 1 weight % to about 4 weight %, about 1.5 weight % to about 3.5 weight %, or about 2 weight % to about 3 weight %. In another implementation, the amount of the one or more plant oils present in the solid cleansing composition may be from greater than 0 weight % to less than or equal to 1 weight %, based on a total weight of the solid cleansing composition. For example, the amount of the one or more plant oils present in the solid cleansing composition may be from greater than 0 weight %, about 0.1 weight %, about 0.2 weight %, about 0.3 weight %, about 0.4 weight %, or about 0.45 weight % to about 0.5 weight %, about 0.6 weight %, about 0.7 weight %, about 0.8 weight %, about 0.9 weight %, or about 1.0 weight %. In another example, the amount of the one or more plant oils present in the solid cleansing composition may be from greater than 0 weight % to about 1.0 weight %, about 0.1 weight % to about 0.9 weight %, about 0.2 weight % to about 0.8 weight %, about 0.3 weight % to about 0.7 weight %, about 0.4 weight % to about 0.6 weight %, or about 0.45 weight % to about 0.5 weight %.

Hydrolyzed Protein

The solid cleansing composition may include one or more hydrolyzed proteins. The hydrolyzed proteins may be completely hydrolyzed or partially hydrolyzed. Illustrative hydrolyzed proteins may be or include, but are not limited to, hydrolyzed gelatin, hydrolyzed collagen, hydrolyzed casein, hydrolyzed whey protein, hydrolyzed milk protein, hydrolyzed soy protein, hydrolyzed egg protein, hydrolyzed wheat protein, amino acids, peptides, and the like, or combinations thereof. In a preferred implementation the hydrolyzed protein includes hydrolyzed milk protein, such as CAS 92797-39-2 (EINECS: 296-575-2). For example, the hydrolyzed protein may be or include a hydrolyzed phosphoprotein derived from natural dairy protein, such as MILK TEIN NPNF®, which is commercially available from Tri-K Industries Inc. of Denville, NJ.

The hydrolyzed milk protein may be or include milk protein hydrolyzed by an enzyme. For example, a milk protein may be enzymatically hydrolyzed to provide the hydrolyzed milk protein.

The hydrolyzed protein may be a solution or mixture. In one implementation, the hydrolyzed protein may be provided as a pure or substantially pure solution. In another implementation, the hydrolyzed protein may be provided as a solution including one or more hydrolyzed proteins dissolved, mixed, or otherwise dispersed in the solution. In at least one implementation, the hydrolyzed protein may be an aqueous solution including the hydrolyzed protein in an amount of from greater than 0 weight % to less than or equal to 50 weight %. For example, a hydrolyzed protein solution may be an aqueous solution including one or more hydrolyzed proteins in an amount of from greater than 0 weight %, about 5 weight %, about 10 weight %, about 15 weight %, about 18 weight %, or about 20 weight % to about 25 weight %, about 30 weight %, about 35 weight %, about 40 weight %, about 45 weight %, or about 50 weight %. In another example, the hydrolyzed protein solution may be an aqueous solution including one or more hydrolyzed proteins in an amount of from greater than 0 weight % to about 50 weight %, about 5 weight % to about 45 weight %, about 10 weight % to about 40 weight %, about 15 weight % to about 35 weight %, about 20 weight % to about 30 weight %, or about 20 weight % to about 25 weight %. In a preferred implementation, the hydrolyzed protein solution is an aqueous solution including about 18 weight % to about 25 weight % of the hydrolyzed protein in water. In a more preferred implementation, the hydrolyzed protein solution is an aqueous solution including about 20 weight % to about 23 weight % of the hydrolyzed milk protein in water.

The amount or concentration of the hydrolyzed protein solution present in the solid cleansing composition may vary widely. In at least one implementation, the amount of the hydrolyzed protein solution (e.g., an about 18 weight % to about 25 weight % or about 20 weight % to about 23 weight % solution of hydrolyzed proteins) present in the solid cleansing composition may be from greater than 0 weight % to less than or equal to 10 weight %, based on a total weight of the solid cleansing composition. For example, the amount of the hydrolyzed protein solution present in the solid cleansing composition may be from greater than 0 weight %, about 1 weight %, about 2 weight %, about 3 weight %, about 4 weight %, or about 5 weight % to about 6 weight %, about 7 weight %, about 8 weight %, about 9 weight %, or about 10 weight %, based on a total weight of the solid cleansing composition. In another example, amount of the hydrolyzed protein solution present in the solid cleansing composition may be from greater than 0 weight %, about 0.2 weight %, about 0.4 weight %, about 0.6 weight %, about 0.8 weight % or about 1.0 weight % to about 1.2 weight %, about 1.4 weight %, about 1.6 weight %, about 1.8 weight %, or about 2.0 weight %, based on a total weight of the solid cleansing composition.

The amount or concentration of the one or more hydrolyzed proteins present in the solid cleansing composition may vary widely. In at least one implementation, the amount of the one or more hydrolyzed proteins present in the solid cleansing composition may be from greater than 0 weight % to less than or equal to 1 weight %, based on a total weight of the solid cleansing composition. For example, the amount of the one or more hydrolyzed proteins present in the solid cleansing composition may be from greater than 0 weight %, about 0.05 weight %, about 0.1 weight %, about 0.15 weight %, about 0.2 weight %, about 0.25 weight %, about 0.3 weight %, about 0.35 weight %, about 0.4 weight %, about 0.45 weight %, or about 0.5 weight % to about 0.55 weight %, about 0.6 weight %, about 0.65 weight %, about 0.7 weight %, about 0.75 weight %, about 0.8 weight %, about 0.85 weight %, about 0.9 weight %, about 0.95 weight %, or about 1 weight %, based on a total weight of the solid cleansing composition. In a preferred implementation, the amount of the one or more hydrolyzed proteins present in the solid cleansing composition may be from about 0.18 weight % to about 0.25 weight %, more preferably about 0.19 weight % to about 0.24 weight %, even more preferably about 0.20 weight % to about 0.23 weight %, based on a total weight of the solid cleansing composition.

The one or more plant oils and/or the one or more hydrolyzed proteins may each be present in an effective or a therapeutically effective amount. As used herein, the expression or term "effective amount" may refer to an amount of the plant oil and/or an amount of the hydrolyzed protein sufficient to elicit a synergistic effect or elicit a response (e.g., biological medical, etc.) of a tissue, system, animal, or human that is being sought. For example, the plant oil and the hydrolyzed protein may each be present in the solid cleansing composition in an effective amount to maintain or increase hydration of skin.

The hydrolyzed protein and the plant oil may be present in a ratio effective or a therapeutically effective ratio to elicit a response (e.g., biological medical, etc.) of a tissue, system, animal, or human that is being sought. For example, the hydrolyzed protein and the plant oil may be present in a weight ratio to maintain or increase hydration of skin. In at least one embodiment, the weight ratio of the plant oil to the hydrolyzed protein may be from about 0.5:1 to about 3.5:1. For example, the weight ratio of the plant oil to the hydrolyzed protein may be from about 0.5:1, about 0.6:1, about 0.7:1, about 0.9:1, about 1.0:1, about 1.1:1, about 1.2:1, about 1.3:1, about 1.4:1, about 1.5:1, about 1.6:1, about 1.7:1, about 1.8:1, about 1.9:1, about 2.0:1, about 2.1:1, or about 2.2:1 to about 2.3:1, about 2.4:1, about 2.5:1, about 2.6:1, about 2.7:1, about 2.8:1, about 2.9:1, about 3.0:1, about 3.1:1, about 3.2:1, about 3.3:1, about 3.4:1, or about 3.5:1. In another example, the weight ratio of the plant oil to the hydrolyzed protein may be from about 1.0:1 to about 3.5:1, about 1.1:1 to about 3.4:1, about 1.2:1 to about 3.3:1, about 1.3:1 to about 3.2:1, about 1.4:1 to about 3.1:1, about 1.5:1 to about 3.0:1, about 1.6:1 to about 2.9:1, about 1.7:1 to about 2.8:1, about 1.8:1 to about 2.7:1, about 1.9:1 to about 2.6:1, about 2.0:1 to about 2.5:1, about 2.1:1 to about 2.4:1, or about 2.2:1 to about 2.3:1. In a preferred implementation, the weight ratio of the plant oil to the hydrolyzed protein may be from about 2.0:1 to about 2.5:1, about 2.1:1 to about 2.4:1, about 2.2:1 to about 2.3:1, preferably about 2.25:1, or more preferably 2.27:1.

Cleansing Component

The solid cleansing composition may include at least one cleansing component. In at least one implementation, the cleansing component may include a base component, such as a soap or a soap chip. The base component or the soap may be or include alkali metal or alkanol ammonium salts of aliphatic alkane- or alkene-monocarboxylic acids, including about 6 to about 22 carbon atoms, about 6 to about 18 carbon atoms, or about 12 to about 18 carbon atoms. Illustrative soaps that may be utilized in the solid cleansing composition may be or include, but are not limited to, sodium soaps, ammonium soaps, potassium soaps, magnesium soaps, calcium soaps, and the like, or mixtures thereof. In a preferred implementation, the base component or soap includes a sodium soap; however, it should be appreciated that at least a portion of the soap may also include one or more ammonium soaps, potassium soaps, magnesium soaps, calcium soaps, and the like, or mixtures and combinations thereof. In a preferred implementation, the base component or the soap may be or include, but is not limited to, alkali metal salts of aliphatic (alkanoic or alkenoic) acids having about 8 to about 22 carbon atoms or about 10 to about 20 carbon atoms.

The base component or soap may be a fatty acid soap. The fatty acid soap may include one or more neutralized fatty acids. Illustrative fatty acids used for the fatty acid soap may be or include, but are not limited to, myristic acid, lauric acid, palmitic acid, oleic acid, stearic acids, and the like, or combinations thereof. Sources of fatty acids may include coconut oil, palm oil, palm kernel oil, tallow, avocado, canola, corn, cottonseed, olive, hi-oleic sunflower, mid-oleic sunflower, sunflower, palm stearin, palm kernel olein, safflower, and babassu oils.

The fatty acids may be neutralized with any base to form the soap or fatty acid soap. Illustrative bases may be or include, but are not limited to, sodium hydroxide, potassium hydroxide, triethanolamine, and the like, or mixtures and combinations thereof. In certain implementations, the fatty acid soap may be formed from fatty acids neutralized by two or more bases. In certain embodiments, the bases are sodium hydroxide and triethanolamine. In certain implementations, the molar ratio of sodium hydroxide and triethanolamine is 1:1. In certain implementations, the fatty acids may be or include any one or more of oleic acid, palmitic acid, stearic acid, and lauric acid. For example, the fatty acid soap may be or include sodium palmitate, sodium oleate, sodium laurate, sodium stearate, or any combination or mixture thereof. In at least one implementation, the fatty acid soap may further include glycerin.

The amount or concentration of the soap in the cleansing component may vary widely. In at least one implementation, the amount of the soap in the solid cleansing component may be greater than or equal to 50 weight % and less than or equal to 95 weight %. For example, the amount of the soap in the solid cleansing component may be from about 50 weight %, about 55 weight %, about 60 weight %, about 65 weight %, or about 70 weight % to about 75 weight %, about 80 weight %, about 85 weight %, about 90 weight %, or about 95 weight %. In another implementation, the amount of the soap in the cleansing component is greater than 70 weight % and less than 80 weight %. For example, the amount of the soap in the solid cleansing component may be from about 70 weight %, about 71 weight %, about 72 weight %, about 73 weight %, about 74 weight %, or about 75 weight % to about 76 weight %, about 77 weight %, about 78 weight %, about 79 weight %, or about 80 weight %. As discussed above, in a preferred implementation, the cleansing component includes a sodium soap. It should be appreciated, however, that the soap of the cleansing composition may include about 1% to about 25% of any one or more of the ammonium soaps, the potassium soaps, the magnesium soaps, the calcium soaps, and the like, and combinations thereof.

The soap of the cleansing component may be or include one or more surfactants. For example, the soap may include one or more anionic surfactants, one or more amphoteric surfactants, one or more cationic surfactants, one or more zwitterionic surfactants, one or more nonionic surfactants, and mixtures thereof. Examples of suitable surfactants may be found in U.S. Pat. No. 3,959,458 to Agricola et al., U.S. Pat. No. 3,937,807 to Haefele, and U.S. Pat. No. 4,051,234 to Gieske et al., the disclosures of which are incorporated herein by reference to the extent consistent with the present disclosure. Any other surfactant may also be present in the soap including, but not limited to, sulfate, sulfonate alpha olefin sulfonates, isethionates such as SCI, N-alkyl or N-acyl taurates, sulfosuccinate, phosphates, glycinates, amphoteric surfactants, such as betaines, sulfobetaines and the like, and nonionic surfactants, such as alkanolamide, alkylpolyglycosides.

Water

The solid cleansing composition and the cleansing component or soap thereof may include water. Water of the solid cleansing composition and the cleansing component thereof may be deionized water, demineralized water, and/or softened water. Water of the cleansing component may be separate from the water of other components of the solid cleansing composition. For example, water of the soap may be separate from water in the hydrolyzed protein solution. Water may make up the balance of the solid cleansing composition. For example, the amount of water in the solid cleansing composition may be from about 1 weight % to about 10 weight %, about 10 weight % to about 20 weight %, about 12 weight % to about 18 weight %, or about 14 weight % to about 16 weight %. In another example, the amount of water in the solid cleansing composition may be at least 10 weight %, at least 11 weight %, at least 12 weight %, at least 13 weight %, at least 14 weight %, at least 15 weight %, at least 16 weight %, or at least 17 weight %. In at least one implementation, the amount of water may be about 10 weight %, about 11 weight %, about 12 weight %, about 13 weight %, about 14 weight %, or about 15 weight %. The amount of water in the solid cleansing composition may include free water added and water introduced with other components or materials of the solid cleansing composition. For example, the amount of water in the solid cleansing composition may include free water and water associated with the soap, the hydrolyzed protein solution, and/or any other component of the solid cleansing composition.

Humectants

The solid cleansing composition may include one or more humectants. Illustrative humectants may include, but are not limited to, ascorbic acid, ascorbyl dipalmitate, acetamide MEA, glucose glutamate, glucuronic acid, TEA-lactate, TEA-PCA, corn syrup, fructose, glucose, glycerin, glycol, 1,2,6-hexanetriol, sodium lactate, sodium PCA, hydrogenated starch hydrolysate, inositol, lactic acid, lactose, mannitol, PCA, PEG-10 propylene glycol, polyamino sugar condensate, propylene glycol, pyridoxine dilaurate, saccharide hydrolysate, hydroxystearyl methylglucamine, glucamine, maltitol, mannitol, methyl gluceth-10, methyl gluceth-20, riboflavin, PEG-4, PEG-6, PEG-8, PEG-9, PEG-10, PEG-12, PEG-14, PEG-16, PEG-18, PEG-20, PEG-32, PEG-40, glutamic acid, glycereth-7, glycereth-12, glycereth-26, saccharide isomerate, sorbeth-20, sorbitol, sucrose, thioglycerin, tris-(hydroxymethyl) nitromethane, tromethamine, histidine, PEG-75, PEG-135, PEG-150, PEG-200, PEG-5 pentaerythritol ether, polyglyceryl sorbitol, sorbitol, urea, xylitol, and the like, and combinations thereof.

Free Fatty Acids

In at least one implementation, the solid cleansing composition may include one or more free fatty acids configured to provide enhanced skin feel benefits. For example, the solid cleansing composition may include the fatty acids to provide softer or smoother feeling skin. Illustrative fatty acids may include, but are not limited to, such as palm kernel oil, palm oil, coconut oil, olive oil, laurel oil, and the like, and combinations thereof. Illustrative fatty acids may also include animal fats, such as tallow. Illustrative fatty acids may also include, but are not limited to, fatty acid sources having fatty acid distributions similar or substantially similar to natural or synthetic fatty acid sources (e.g., natural animal fats or oils, natural vegetable fats or oils, individual fatty acids, etc.). The free fatty acids may be separate from the fatty acids associated with the plant oils.

Skin Care Agents

The solid cleansing composition may include one or more skin care agents. Any suitable skin care agents that do not adversely affect the stability and/or efficacy of the solid cleansing composition may be used. In at least one implementation, the skin care agent may include an emollient configured to maintain a soft, smooth, and pliable appearance to the skin. As is known by those skilled in the art, the emollients may function by remaining on the surface of the skin or in the stratum corneum to act as a lubricant, to reduce flaking, and/or to improve the appearance of the skin.

The skin care agents may generally include one or more polymers (e.g., polyvinylpyrrolidine), protein derivatives (e.g., derivatized hydrolyzed wheat protein), ethoxylated fatty ethers, cellulosics (e.g., hydroxyethylcellulose), and the like, or mixtures and combinations thereof. Illustrative skin care agents may include, but are not limited to, esters comprising an aliphatic alcohol having about 2 to about 18 carbon atoms condensed with an aliphatic or aromatic carboxylic acid including about 8 to about 20 carbon atoms (e.g., isopropyl myristate, decyl oleate, cetearyl isononanate, etc.). The esters may be straight chained or branched. In a preferred implementation, the ester has a molecular weight of less than about 500.

Other skin care agents may include, but are not limited to, polyvinyl-pyrrolidone, polyquaternium-4, polyquaternium-7, polyquaternium-10, guar gum derivatives, hydroxypropylmethylcellulose, hydroxyethylcellulose, a polyethylene glycol, a methyl ether of a polyethylene glycol, quaternium-79, wheat germamidopropyl hydroxypropyl dimonium hydrolyzed wheat protein, stearyl methicone, dimethicone copolyol, dimethicone propyl PG betaine, poly(sodium styrene sulfonate), sorbitan oleate, steareth-2, steareth-21, isoceteth-20, PEG-7 glyceryl cocoate, PEG-75 lanolin, glycereth-26, PPG-5-ceteth-20, a C12-C20 alcohol, canola oil, glyceryl laurate, triglyceryl monostearate, glyceryl monostearate, vitamin E acetate, sunflower seed amidopropylethyldimonium ethylsulfate, sodium PEG-7 olive oil carboxylate, PPG-1 hydroxyethyl caprylamide, PPG-2 hydroxyethyl cocamide, mineral oil, petrolatum, aloe barbadensis, isostearamidopropylmorpholine lactate, strontium acetate, palmitamidopropyltrimonium chloride, and the like, and combinations thereof. In a preferred implementation, the skin care agent is or includes a conditioner, such as a cationic cellulose polymer (e.g., polyquaternium-7).

Salts

The solid cleansing composition may include one or more salts configured to modify the one or more surfactants of the solid cleansing composition. For example, the salts may be configured to at least partially modify a cloud point of the surfactants to thereby control the haze or transparency of the cleansing composition. The salts may be or include one or more inorganic salts including, but not limited to, sodium sulfate, magnesium sulfate, sodium chloride, sodium citrate, and the like, and combinations thereof. The amount of any one or more of the salts may be at least partially determined by the type and/or amount of the surfactants included in the solid cleansing composition. In at least one implementation, the amount of any one or more of the salts may be about 0.1 weight %, 0.2 weight %, 0.3 weight %, 0.4 weight %, or 0.5 weight % to about 0.6 weight %, 0.7 weight %, 0.8 weight %, 0.9 weight %, or about 1.0 weight %.

Additional Optional Components/Ingredients

The solid cleansing composition may include one or more additional optional ingredients. Illustrative optional ingredients may include, but are not limited to, one or more dyes, fragrances (e.g., limonene, ethyl butyrate, linalool, and/or oils, such as citronellol, coumarin, benzyl salicylate, etc.), buffers and buffering agents (e.g., inorganic phosphates, sulfates, and carbonates), pH adjusters (e.g., acids and/or bases), preservatives (e.g., parabens, hydantoins, imidazolines, etc.), thickeners, viscosity modifiers, antioxidants (e.g., etidronic acid, etc.), foam enhancers, chelating agents (e.g., EDTA, phosphates, pentasodium pentetate, etidronic acid, etc.), skin conditioning agents, opacifiers, hydric solvents, hydrotropes, antimicrobials (e.g., trichlorocarbanilide (TCC), triclosan, geraniol, carvacrol, citral, eucalyptol, catechol, 4-allylcatechol, hexyl resorcinol, methyl salicylate, etc.), sunscreen actives, anti-aging compounds, vitamins, essential oils and extracts (e.g., rosewood, jojoba, etc.), polyols, titanium dioxide, abrasives (e.g., particulate matter), acaricidal agents (e.g., benzyl benzoate), and the like, and combinations thereof.

Illustrative antimicrobials may include, but are not limited to, triclocarban, triclosan, and the like, and combinations thereof. Illustrative anti-aging compounds may include, but are not limited to, alpha hydroxy acids, beta hydroxy acids, and the like, and combinations thereof. Illustrative sunscreen actives may include, but are not limited to, butyl methoxy benzoylmethane, and the like, and combinations thereof. Illustrative polyols may include, but are not limited to, glycerol, sorbitol, propylene glycol, polyethylene glycol, and the like, and combinations thereof. Illustrative abrasives or particulate matter may include, but are not limited to, silica, talc, calcium carbonate, polyethylene beads, jojoba beads, lufa, oat flour, and the like, and combinations thereof. Illustrative vitamins may include, but are not limited to, vitamins such as vitamin A, E, K, and C.

Illustrative basic pH adjusters may include, but are not limited to, ammonia; mono-, di-, and tri-alkyl amines; mono-, di-, and tri-alkanolamines; alkali metal and alkaline earth metal hydroxides; and the like, and combinations thereof. For example, the basic pH adjuster may be ammonia, sodium hydroxide, potassium hydroxide, lithium hydroxide, monoethanolamine, triethylamine, isopropanolamine, diethanolamine, triethanolamine, and the like, and combinations thereof.

Illustrative acidic pH adjusters may include mineral acids and polycarboxylic acids. The mineral acids may be or include hydrochloric acid, nitric acid, phosphoric acid, sulfuric acid, and the like, and combinations thereof. The polycarboxylic acids may be or include citric acid, glycolic acid, lactic acid, and the like, and combinations thereof.

The preservatives may be included in the solid cleansing composition in an amount greater than 0.00 weight % and less than or equal to about 3.0 weight % or about 2.0 weight %. Illustrative preservatives may include, but are not limited to, benzalkonium chloride; benzethonium chloride, 5-bromo-5-nitro-1,3-dioxane; 2-bromo-2-nitropropane-1,3-diol; alkyl trimethyl ammonium bromide; N-(hydroxymethyl)-N-(1,3-dihydroxy methyl-2,5-dioxo-4-imidaxolidinyl-N-(hydroxy methyl)urea; 1-3-dimethyol-5,5-dimethyl hydantoin; formaldehyde; iodopropynl butyl carbamate; butyl paraben; ethyl paraben; methyl paraben; propyl paraben, mixture of methyl isothiazolinone/methyl-chloroisothiazoline in a 1:3 wt. ratio; mixture of phenoxythanol/butyl paraben/methyl paraben/propylparaben; 2-phenoxyethanol; tris-hydroxyethyl-hexahydrotriaz-ine; methylisothiazolinone; 5-chloro-2-methyl-4-isothiazolin-3-one; 1,2-dibromo-2,4-dicyanobutane; 1-(3-chloroalkyl)-3,5,7-triaza-azoniaadam-antane chloride; sodium benzoate; organic acids, sorbic acid, lactic acid, citric acid, and the like, and combinations thereof.

Solid Cleansing Composition

In an exemplary implementation, the solid cleaning composition includes a cleansing component, such as a sodium soap including any one or more of sodium palmitate, sodium oleate, sodium laurate, sodium stearate, and glycerin. The solid cleansing composition further includes water, glycerin, one or more perfumes or fragrances, one or more hydrolyzed proteins, one or more plant seed oils, titanium dioxide, etidronic acid, pentasodium pentetate, limonene, citronellol, coumarin, benzyl benzoate, geraniol, linalool, benzyl salicylate, or any combination thereof. In at least one implementation, the solid cleansing composition may increase hydration of skin as compared to the same or a similar solid cleansing composition without the hydrolyzed protein (hydrolyzed milk protein) and the plant seed oil (flaxseed oil).

Methods

The present disclosure may provide methods for preparing a personal care composition, such as a solid cleansing composition. The method for preparing the solid cleansing composition may include contacting synergistic amounts of one or more plant oils and one or more hydrolyzed proteins with one another. The method may also include contacting soap, one or more plant oils, and one or more hydrolyzed proteins with one another. The one or more plant oils may be or include flaxseed oil, and the one or more hydrolyzed proteins may be or include hydrolyzed milk protein. In another example, the one or more plant oils may be or include flaxseed oil, and the one or more hydrolyzed proteins may be or include an aqueous solution including hydrolyzed milk protein (e.g., about 18 weight % to about 25 weight % or about 20 weight % to about 23 weight % aqueous solution of hydrolyzed milk protein).

The present disclosure may also provide methods for maintaining or increasing hydration of skin. The present disclosure may further provide methods for treating one or more dry skin conditions (e.g., xerosis, psoriasis, etc.). The method may include contacting surfaces of the skin with a solid cleansing composition including a synergistic amount of one or more plant oils and one or more hydrolyzed proteins. The method may also include combining the synergistic amount of the plant oils and the hydrolyzed proteins with a carrier, such as a soap. The one or more plant oils may be or include flaxseed oil, and the one or more hydrolyzed proteins may be or include hydrolyzed milk protein. In another example, the one or more plant oils may be or include flaxseed oil, and the one or more hydrolyzed proteins may be or include an aqueous solution including hydrolyzed milk protein (e.g., about 18 weight % to about 25 weight % or about 20 weight % to about 23 weight % aqueous solution of hydrolyzed milk protein).

The present disclosure may further provide a use of a solid cleansing composition including a soap, one or more plant oils, and one or more hydrolyzed proteins for maintaining or increasing hydration of skin. The present disclosure may also provide a use of a solid cleansing composition including a soap, one or more plant oils, and one or more hydrolyzed proteins for treating one or more dry skin conditions (e.g., xerosis, psoriasis, etc.). The one or more plant oils may be or include flaxseed oil, and the one or more hydrolyzed proteins may be or include hydrolyzed milk protein. In another example, the one or more plant oils may be or include flaxseed oil, and the one or more hydrolyzed proteins may be or include an aqueous solution including hydrolyzed milk protein (e.g., about 18 weight % to about 25 weight % or about 20 weight % to about 23 weight % aqueous solution of hydrolyzed milk protein).

EXAMPLES

The examples and other implementations described herein are exemplary and not intended to be limiting in describing the full scope of compositions and methods of this disclosure. Equivalent changes, modifications and variations of specific implementations, materials, compositions and methods may be made within the scope of the present disclosure, with substantially similar results.

Example 1

A base bar soap composition or control (1) in the form of a plurality of soap chips was prepared by combining the ingredients/components according to Table 1. Three test bar soap compositions (2)-(4) were then prepared by adding varying amounts of flaxseed oil and hydrolyzed milk protein solution (MILK TEIN NPNF®; about 18 weight % to about 25 weight % hydrolyzed milk protein in water) to the control, according to Table 2. The hydrolyzed milk protein solution (MILK TEIN NPNF®) was obtained from Tri-K Industries, Inc. of Denville, NJ.

TABLE 1

Composition of Base Bar Soap Composition

| Ingredient/Component | Amount (wt %) |
|---|---|
| Soap chips containing sodium palmitate, sodium oleate and sodium laurate | 76.3 |
| Glycerin | 7.3 |
| Demineralized water | 15 |
| Perfume | 1.4 |

TABLE 2

Compositions of Control and Test Bar Soap Compositions (1) - (4)

| # | Base Bar Soap Composition (wt %) | Flaxseed Oil (wt %) | Hydrolyzed Milk Protein Solution (wt %) |
|---|---|---|---|
| (1) Control | 100.0 | 0.0 | 0.0 |
| (2) | 99.5 | 0.5 | 0.0 |
| (3) | 99.0 | 0.0 | 1.0 |
| (4) | 98.5 | 0.5 | 1.0 |

Example 2

Each of the control (1) and test (2)-(4) bar soap compositions was studied in vitro with skin tissue models to evaluate the hydration properties thereof. Pigskins were used as the skin models for each of the bar soap compositions (1)-(4). Particularly, 1.5 square inch samples of pig skin were cut from the same piece of pig skin and separated into four test group to test each of the four bar soap composition (1)-(4). Each of the bar soap compositions (1)-(4) was used to treat twelve pig skin models. To evaluate the hydration properties, a pig skin was placed in a petri dish and wetted under running water maintained at about 95° F. (about 35° C.) for several seconds. One of the bar soap compositions (1)-(4) was then rotated by hand under the running water maintained at about 95° F. (about 35° C.) for about 5 seconds. The wetted bar soap composition (1)-(4) and the wetted pig skin were then contacted with one another for about 10 seconds, and subsequently lathered with a gloved finger for about 15 seconds. The resulting lather was left on the skin for about 30 seconds prior to rinsing under the water (about 95° F. or about 35° C.) for about 15 seconds. The rinsed pig skin was then dried in air for about 30 minutes. The process was repeated two more times to provide a total of three washing treatments. After the pig skin was exposed to three washing treatments, the pig skin was stored overnight at about 40% relative humidity (RH) at about 70° F. (about 21° C.).

After storing overnight, water content measurements or hydration properties of each of the bar soap compositions (1)-(4) on the skin models were quantified via confocal Raman spectroscopy or microscopy (Model 3510 from River Diagnostics, Rotterdam, the Netherlands). The water concentration (weight %) of skin was measured to a depth of 50 μm in 2 μm increments. The acquisition time was 1 second/step in the spectral region of from about 2500 cm$^{-1}$ to about 4000 cm$^{-1}$. The concentration of water (weight %) was determined automatically through the built-in software provided by the instrumentation and a water profile curve that was obtained.

The results of the water content measurements or hydration properties of each of the bar soap compositions (1)-(4) on the skin models were obtained via integration of a water profile curve (area under the curve) and are summarized in Table 3.

TABLE 3

| Water Content Measurements of Bar Soap Compositions (1)-(4) | | | |
| --- | --- | --- | --- |
| # | Average Water Content (weight %) | Std Dev. | Δ Water Content vs. Control (%) |
| (1) Control | 2615 | 275.4 | — |
| (2) 0.5 wt % Flaxseed Oil | 2589 | 302.5 | −26 |

TABLE 3-continued

| Water Content Measurements of Bar Soap Compositions (1)-(4) | | | |
| --- | --- | --- | --- |
| # | Average Water Content (weight %) | Std Dev. | Δ Water Content vs. Control (%) |
| (3) 1% of Hydrolyzed Milk Protein Solution (providing about 0.18% to about 0.25% Hydrolyzed Milk Protein, based on a total weight of the bar soap composition) | 2601 | 235.2 | −14 |
| (4) 0.5 wt % Flaxseed Oil and 1 wt % Hydrolyzed Milk Protein Solution (providing about 0.18% to about 0.25% Hydrolyzed Milk Protein, based on a total weight of the bar soap composition) | 2755 | 214.8 | +140 |

As illustrated in Table 3, the bar soap composition including 0.5 wt % flaxseed oil (2) decreased water content or hydration of skin relative to the control (1). Similarly, the bar soap composition including 1 weight % of hydrolyzed milk protein (3) decreased water content or hydration of skin relative to the control (1). As such, it was surprisingly and unexpectedly discovered that the bar soap composition including a combination of flaxseed oil and hydrolyzed milk protein (4), both of which individually decreased the relative water content or hydration of skin, significantly increased the hydration of skin relative to the control (1). Further, the ability to increase the hydration of skin in a bar soap was surprising and unexpected, as bar soaps generally dry skin, as opposed to liquid cleansing compositions (e.g., shower gels), which are generally capable of increasing hydration of skin.

The present disclosure has been described with reference to exemplary implementations. Although a limited number of implementations have been shown and described, it will be appreciated by those skilled in the art that changes may be made in these implementations without departing from the principles and spirit of the preceding detailed description. It is intended that the present disclosure be construed as including all such modifications and alterations insofar as they come within the scope of the appended claims or the equivalents thereof.

What is claimed is:

1. A solid cleansing composition comprising a soap, a plant oil, and hydrolyzed milk protein, wherein the plant oil and the hydrolyzed milk protein are present in an effective amount to maintain or increase hydration of skin; wherein the plant oil is flaxseed oil which is present in an amount of 0.4 wt. % to 0.6 wt. % and the hydrolyzed milk protein is present in an amount of from 0.18 wt. % to 0.25 wt. %, based on the total weight of the solid cleansing composition.

* * * * *